(12) United States Patent
Martinsen et al.

(10) Patent No.: US 7,848,798 B2
(45) Date of Patent: Dec. 7, 2010

(54) LIVE FINGER DETECTION BY FOUR-POINT MEASUREMENT OF COMPLEX IMPEDANCE

(75) Inventors: Ørjan G. Martinsen, Stabekk (NO); Jon Nysæther, Oslo (NO); Knut Riisnæs, Oslo (NO); Ingvild Juvkam Dyve, legal representative, Oslo (NO); Geir Mostad, Oslo (NO); Rune Pedersen, Heggedal (NO); Nicolai W. Christie, Hosle (NO); Sigmund Clausen, Oslo (NO)

(73) Assignee: Idex ASA, Fornebu (NO)

( * ) Notice: Subject to any disclaimer, the term of this patent is extended or adjusted under 35 U.S.C. 154(b) by 1479 days.

(21) Appl. No.: 10/537,508

(22) PCT Filed: Dec. 3, 2003

(86) PCT No.: PCT/NO03/00405

§ 371 (c)(1),
(2), (4) Date: Jul. 18, 2005

(87) PCT Pub. No.: WO2004/049942

PCT Pub. Date: Jun. 17, 2004

(65) Prior Publication Data

US 2005/0281441 A1 Dec. 22, 2005

(30) Foreign Application Priority Data

Dec. 3, 2002 (NO) .................................. 20025803

(51) Int. Cl.
*A61B 5/05* (2006.01)
*G06T 1/00* (2006.01)
*G06T 7/00* (2006.01)

(52) U.S. Cl. .................................. 600/547; 340/5.83

(58) Field of Classification Search ................ 600/506, 600/547; 340/5.53, 5.83
See application file for complete search history.

(56) References Cited

U.S. PATENT DOCUMENTS

| 4,540,002 | A | 9/1985 | Atlas et al. |
| 4,966,158 | A | 10/1990 | Honma et al. |

(Continued)

FOREIGN PATENT DOCUMENTS

EP 0 315 854 A1 5/1989

(Continued)

*Primary Examiner*—Max Hindenburg
*Assistant Examiner*—Jonathan M Foreman
(74) *Attorney, Agent, or Firm*—Rothwell, Figg, Ernst & Manbeck, PC

(57) ABSTRACT

Method and sensor assembly determining the condition of a structure, especially for confirming if a measured fingerprint is on a live finger, by measuring characteristics of close to the structure surface, the sensor comprising a first pair of current supply electrodes coupled to a current source, providing an electrical current to the skin, at least two pickup electrodes at chosen and different positions relative to the current supply electrodes, at least a first of said pickup electrodes being coupled to an instrument for measuring the voltage between said first pickup electrode and at least one of the pickup or current supply electrodes, storage means for a predetermined set of values characterizing a certain condition of the surface, and means for comparing the characteristics from each pickup electrode with the measurements of the other pickup electrodes and with the predetermined set of characteristics for determining the surface condition.

4 Claims, 4 Drawing Sheets

U.S. PATENT DOCUMENTS

| | | |
|---|---|---|
| 5,807,270 A | 9/1998 | Williams |
| 5,953,441 A | 9/1999 | Setlak |
| 6,321,112 B1 * | 11/2001 | Masuo ....................... 600/547 |
| 2001/0005424 A1 | 6/2001 | Marksteiner |

FOREIGN PATENT DOCUMENTS

| | | |
|---|---|---|
| JP | 2001-104274 A | 4/2001 |
| WO | WO 96-10951 A1 | 4/1996 |
| WO | WO 97-14111 A1 | 4/1997 |
| WO | WO 99-23945 A1 | 5/1999 |
| WO | WO 00-19894 A1 | 4/2000 |
| WO | WO 01-56468 A2 | 8/2001 |
| WO | WO 03-094724 A1 | 11/2003 |

\* cited by examiner

LIVE FINGER DETECTION BY FOUR-POINT MEASUREMENT OF COMPLEX IMPEDANCE

CROSS REFERENCE TO RELATED APPLICATIONS

This application is a 35 U.S.C. §371 National Phase Entry Application from PCT/NO3/00405, filed Dec. 3, 2003.

BACKGROUND OF THE INVENTION

1. Field of the Invention

This invention relates to a sensor assembly and method for determining the condition of a structure, especially for confirming if a measured fingerprint is on a live finger, by measuring characteristics of close to the structure surface.

2. Introduction

Capacitance or impedance based fingerprint sensors are some of the most promising approaches to offer a low-cost, miniaturized device for biometric identification. Such sensors are therefore possible candidates for integration in mobile phones etc.

To enhance the trust of fingerprint sensors, it is of great importance that any attempt to fool the system by using fake fingers may be detected and rejected. A fake finger will typically consist of a slab of material with electrical properties resembling that of a finger, and with a fingerprint carved or molded into its surface. In a more extreme case one may also imagine that a dead, cut-off finger may be used.

For live finger detection systems, it is important both that the probability of accepting a false finger (false acceptance ratio—FAR) and the probability of rejecting a real finger (false rejection ratio—FRR) are extremely low. This makes it important to develop a method for identifying very characteristic and unique properties of a living finger, properties that can not easily be replicated by either synthetic materials or by other biological substance than living tissue, and which are typical of the vast majority of fingers in the population.

For low cost capacitive based fingerprint sensors some kind of impedance measurement of the finger properties will be ideal, as it can most often be integrated directly on the device by using existing measurement structures or adding a number of extra electrodes.

PRIOR ART

Several different types of fingerprint sensors have recently been developed, from 2-dimentional matrix sensors as described in U.S. Pat. No. 5,953,441 through sensor arrays reconstructing the fingerprint image from series of semi-overlapping partial images in U.S. Pat. No. 6,289,114 to linear sensors as described in EP 0988614 which scans the finger surface and uses the measured finger velocity to reconstruct the finger image.

Attempts to detect live fingers include both blood oxygenation and blood pulse measurements. However, as the blood circulation in the finger may be virtually non-present in very cold fingers, these methods are far from being "water-proof". Neither are these principles easy to implement on a low cost device.

U.S. Pat. Nos. 6,175,641, 5,953,441 and patent application US2001/0005424 A1 all show different impedance based methods of investigating whether an object which is placed on a fingerprint sensor corresponds to a live finger.

U.S. Pat. No. 6,175,641, which relates to impedance sensing on an optical matrix sensor, shows two different methods for measuring the electrical characteristics of the finger: Firstly, the dielectric constant is measured locally by applying an AC signal between two closely spaced electrode comb structures on the sensor surface. It is claimed that this measurement can separate living tissue (high dielectric constant) from commercial plastics (low dielectric constant).

Secondly, the sensor has a so-called double dot electrode for determining the impedance of the finger, which presumably will give additional information that can be used to distinguish real fingers from fake. The patent also mentions the use of several frequencies to increase the security of the measurement.

The method described in this patent however has a number of weaknesses. While the dielectric measurement will perhaps work well for dry fingers, for sweat or humid fingers the closely spaced comb structures will most probably be short-circuited by saline sweat, and no useful information will be obtained.

In addition the impedance of a living finger, as measured by the double dot system, may vary with at least one order of magnitude depending on the humidity of the finger. It is therefore difficult to use this as criteria to identify a finger, and both the impedance magnitude, its phase and its variation with frequency could probably be faked by simple well-known materials from everyday life, such as a peeled potato.

U.S. Pat. No. 5,953,441 describes spoof detection for an AC capacitive fingerprint sensor containing a matrix of capacitive sensing elements. The main idea for live finger detection is here to send AC signal through an electrode around the rim of the sensor area, and to detect the phase of the signals on the sensor elements, this phase being characteristic of a living finger.

However, while this method will rule out a number of different fake finger materials, it will be relatively easy to find a material that gives approximately the same phase as a finger, and thereby to fool the system. Patent application US2001/0005424 A1 shows a method resembling the method described in U.S. Pat. No. 6,175,641. The impedance of the finger (either between two electrodes or between one electrode and "infinity") is measured as a function of frequency. By comparing the curve to a reference curve the living characteristics of a finger may then be detected. This method however adds little to the methods described above. The absolute impedance and frequency response between different fingers, and between different states (e.g with respect to humidity) of the same finger, differ so much that the "live finger criteria" would have to be very wide, and so the principle would be easy to fool.

International patent application PCT/NO03/00157 (WO03094724), hereby included here by way of reference, shows another live finger detection principle, based on four point measurements of complex impedance. Here, an AC current or voltage is applied between two electrodes while measuring the voltage drop between two other electrodes, all electrodes being in contact with the finger surface. The four-point principle, applied to finger impedance measurements, is visualized in FIG. 1. An AC current is sent through the finger through the outer electrodes, while the voltage drop is measured between the two inner electrodes using a differential amplifier.

SUMMARY OF INVENTION

The aim of the current invention is to ensure a four-point measuring system for live finger detection that can be used to compensate for differences in finger characteristics among a population, such as a varying stratum corneum thickness.

To reach this aim, the proposed invention consists of an impedance measuring system with an array of at least four electrodes. The electrodes may be in direct contact with or capacitively coupled to the finger through an insulating layer. The electrodes are arranged in such a way that they can be used in at least two different four-point electrode configurations, corresponding to different relative placements between the current and voltage sensing electrodes. The objects of this invention is obtained as described in the accompanying claims.

The use of a four point technique makes it possible to cancel out the series impedance of the horny layer, thus directly measuring the impedance of the finger interior. The impedance of the horny layer is extremely dependent on the humidity of the skin and on ambient conditions such as temperature. This makes it difficult to identify "narrow" criteria that may be used to separate real fingers from fake. In contrast, the humidity of finger interior remains fairly constant under varying ambient conditions. The impedance of the finger interior (living skin and tissue) is therefore far more constant, and more reproducible from person to person.

The four-point principle will thus make it easier to obtain "narrow" criteria that can be used for identifying whether a finger is a real and live finger.

Because of the layered structure of the skin, the four point principle also gives an inherent "depth selectivity": By increasing the frequency the measurement is influenced by still deeper portions of the living skin. This makes it possible to measure depth-specific variations in the electrical properties merely by carrying out a frequency sweep.

The living tissue of the finger interior also has very characteristic dispersions (variation in electrical properties with frequency) that can be used to identify a real finger with a high degree of security. These properties change after death or when a finger is cut off from the hand, and makes it possible also to determine whether the finger is live.

One weakness of the principle proposed in PCT/NO03/00157 (WO03094724), is that the four-point impedance is that the impedance is measured with only one set of electrodes where all electrodes have a fixed distance.

Depending on the relative positions of the electrodes of the four-point structure, the impedance measurements will however be more or less affected by the stratum corneum (horny layer).

In the limit of a very short distance between the current electrodes, the current will not penetrate into the living skin of the finger interior at all, thus giving a measurement only of the stratum corneum alone.

In the other limit, with a large electrode distance, the measurement will be largely determined by the properties of the living tissue of the finger interior.

Because different people have different stratum corneum thicknesses, a fixed electrode distance will give different results for different people, thus making it difficult to identify a living finger without using very wide criteria. If the criteria are not narrow enough, the principle will be easier to spoof.

It will be known to the skilled engineer that different electrode configurations, where the electrodes have different relative placements, corresponds to the measurement of different portions of the object adjacent the electrodes. The portion of a finger that is measured by the four-point principle is however not only determined by the distance between the two current sensing electrodes and between the two voltage sensing electrodes, but also on the electrode geometry and the relative placement of the voltage sensing electrodes with respect to the current electrodes.

By activating different electrodes in the array or by interchanging the role (voltage sensing or current) of electrodes already in use, it can therefore be switched between different four point electrode configurations.

By switching between a number of different electrode configurations within the array it will thus be possible to measure sections of the finger e.g. corresponding to different measuring depths, and thus compensate for variations in e.g. stratum corneum thickness.

To exemplify, a characteristic dispersion (shift in complex impedance with frequency) that is observed for one person using one electrode arrangement, may be detected for another person using another arrangement.

To reveal the same dispersion, a person with a very thick stratum corneum may for instance require a larger distance between the current injection or voltage sensing electrodes than a person with a thin stratum corneum.

A minimum criterion for accepting an object as a live finger may be that at least one specific, impedance related phenomenon is detected for at least one of the electrode arrangements.

It should be emphasized that the focus on "differences in stratum corneum thickness" is only exemplatory. The principle applies to all properties of the finger where a shift in electrode geometry may help to reveal certain impedance related phenomena within a given frequency range.

Preferably, to enhance the security of detecting a live finger across a significant population, the number of possible electrode configurations may be higher than two, for instance 3-5. The various configurations can of course be arranged in the form of separate arrays so that a minimum of switching is required.

BRIEF DESCRIPTION OF THE DRAWINGS

The invention will be described below with reference to the accompanying drawings, illustrating the invention by way of examples.

PRACTICAL IMPLEMENTATION

Figure 1:
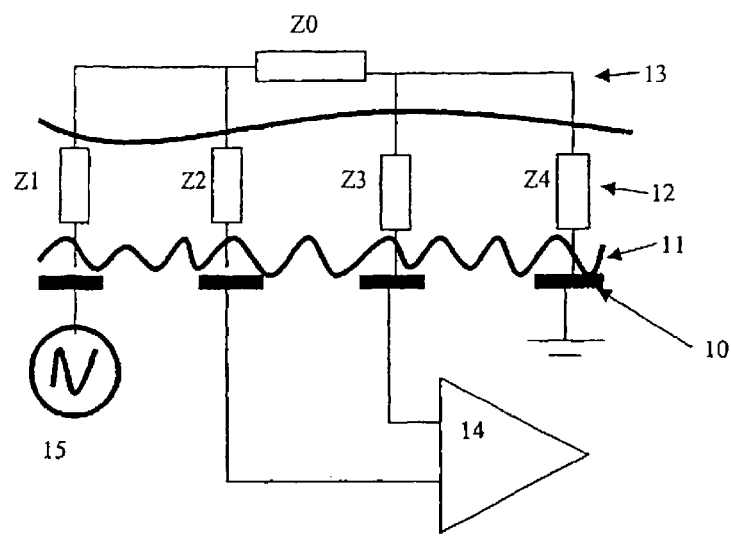
FIG. 1 illustrates the electrical equivalent of the two layer structure being interrogated by a sensor assembly according to the invention.

In FIG. 1 a finger surface 11 is positioned on a number of sensors 10. The finger structure comprises two layers, the stratum corneum 12 and the live live tissue 13 of the live finger. The stratum corneum (horny layer) 12 constitutes impedances Z1, Z2, Z3 and Z4, respectively, at each of the four illustrated electrodes 10, while the living tissue represents the impedance Z0.

In a practical device, a four-point measurement may be implemented by an array of electrodes on the sensor surface, e.g. defined in thin film, thick film or printed circuit board technology. The electrodes may either give a galvanic contact with the finger or be passivated with a thin dielectric to give a pure capacitive coupling from electrode to finger.

A typical size of the individual electrodes (both current and voltage electrodes) will be 0.5-5 mm$^2$, and a typical minimum electrode spacing will be 0.3-2 mm.

Figure 2:
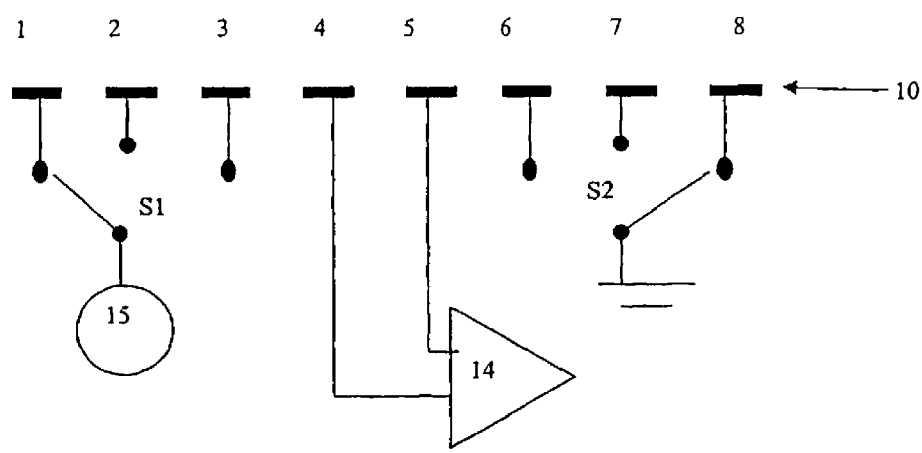
FIG. 2 illustrates one possible configuration for switching the roles of a number of electrodes according to the invention.

FIG. 2 shows an example of how an array of 8 electrodes can be arranged to allow for measurements at a number of different current electrode distances. In this structure, the voltage measurements are always performed between the electrodes 4 and 5, while the two switches S1 ans S2 are used to make different combinations of the electrodes 1,2,3 (AC source) with the electrodes 6,7 and 8 (AC drain or ground), and thereby vary the current electrode distance. Alternatively, the role of the current and voltage sensing electrodes can be interchanged so that current is always sent between the innermost electrodes and the voltage measurement is switched between various combinations of the remaining electrodes. It is known from prior art that if the role of the voltage sensing pair is interchanged with the current electrode pair, the measured impedance remains essentially the same.

By choosing the range of inter-electrode distances corresponding to stratum corneum thickness variations in the population (or other variations that give corresponding effects, such as differences in humidity), it will be possible to obtain information that can be compared more directly and thus used to "narrow" the criteria for a real finger. This will enable live finger identification with a higher degree of certainty than any of the above described methods.

In designing the read-out system, it is important to maximize the input impedance in the voltage sensing branches, as too low impedance will give rise to a parasitic input current that influences on the measuring principle. To minimize the effect of input impedances, an amplification coupling as described in U.S. Pat. No. 4,956,729 can be employed. The input current to a voltage pad can also be minimized by shielding the input pad (and the track connecting it with the amplifier) by an electrode having the same voltage as the input pad itself ("active shield"). Such a voltage is readily obtained by a simple voltage follower stage where the input voltage is fed back to the shielding electrode.

If the input impedance of the amplifier is sufficiently high (or equivalently, if the input current is sufficiently low), the detected voltage will not be influenced by the impedances Z2, Z3, Z1 and Z4 through the horny layer, but only by Z0, being characteristic of the finger interior.

It should be emphasized that the disclosed system in figure is only one possible way the electrodes can be arranged. In principle, all electrode arrangements yielding two or more different electrode configurations can be used. For voltage or impedance sensing, the fingerprint sensor elements themselves can be used.

Upon live finger detection, four-point complex impedance measurements are obtained for each of the electrode arrangements for a single frequency or across a range of frequencies. For instance, the properties can be measured continuously with frequency or at a number of different discrete frequencies. The frequency span is preferably 1-3 orders of magnitude.

By measuring the amplitude of the current through the finger and the differential voltage in at least two different time instants during a signal cycle, the reactance X0 and resistance R0 of the complex impedance Z0=R0+jX0 can be determined for each frequency. Other techniques for detecting the components of the complex impedance may also be used.

Live finger data will preferably be recorded right before, right after or most preferably, during the course of fingerprint image capturing. This makes it difficult to spoof the system by first applying a real finger and then a fake finger with the correct fingerprint pattern. In some systems, the live finger detection and fingerprint imaging may not be done at the same time due to conflicting signals. In this case, it is possible to suspend the fingerprint imaging for short time intervals and carry out the live finger detection within this time frame. It is then important that the time for live finger detection is short enough to avoid affecting image quality significantly.

For a sweep sensor of the type described in EP 0988614 this could be accomplished by skipping e.g. one or two lines of image data and perform the live finger detection during this time. As mentioned above this solution comprises a number of sensor elements for measuring the impedance between a stimulation electrode and the sensor elements. According to the present invention the role of the sensor elements may be altered for one or a few measuring periods for measuring the condition of the finger. As the solution described in the above-mentioned application allows for over sampling and rejection of unnecessary data the live finger detection mode should not be noticeable in the resulting fingerprint image.

In this case it is also important that the geometrical area used for live finger detection overlaps the area used for fingerprint imaging, so that one can be certain that the detected live finger and the imaged objects are indeed the same.

As previously described, the criterion for accepting an object as a live finger may be based on measurements of at least one impedance related parameter from at least one of the electrode configurations.

This parameter may e.g. be a value or combination of values related to the measured impedance, such as the phase, magnitude, resistance or reactance, or it may be a variation of some value with respect to frequency. The parameter may also be some derived value, e.g. the frequency at which some parameter attains a certain value.

In a preferred embodiment, at least one of these parameters is related to an observed phase change of the measured 4-point finger impedance taking place in the frequency range between approximately 10 kHz and 1 MHz. In this frequency range, the finger impedance phase has been seen to undergo a shift of 50-90 degrees as the dominating part of the impedance changes from capacitive to resistive.

The change from a dominating capacitive to a resistive impedance is also seen as a change in the frequency derivative of the impedance magnitude, which changes from negative to around zero when frequency passes a typical frequency.

Figure 4:
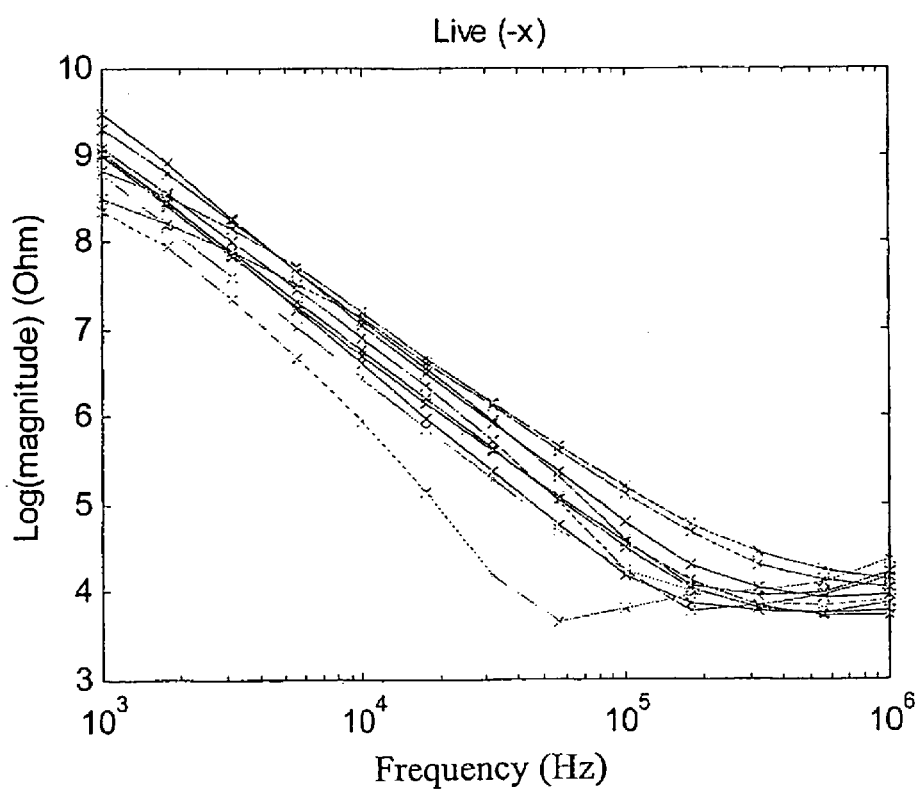
FIG. 4 shows the measured impedance absolute value as a function of frequency for a first electrode configuration.
Figure 5:
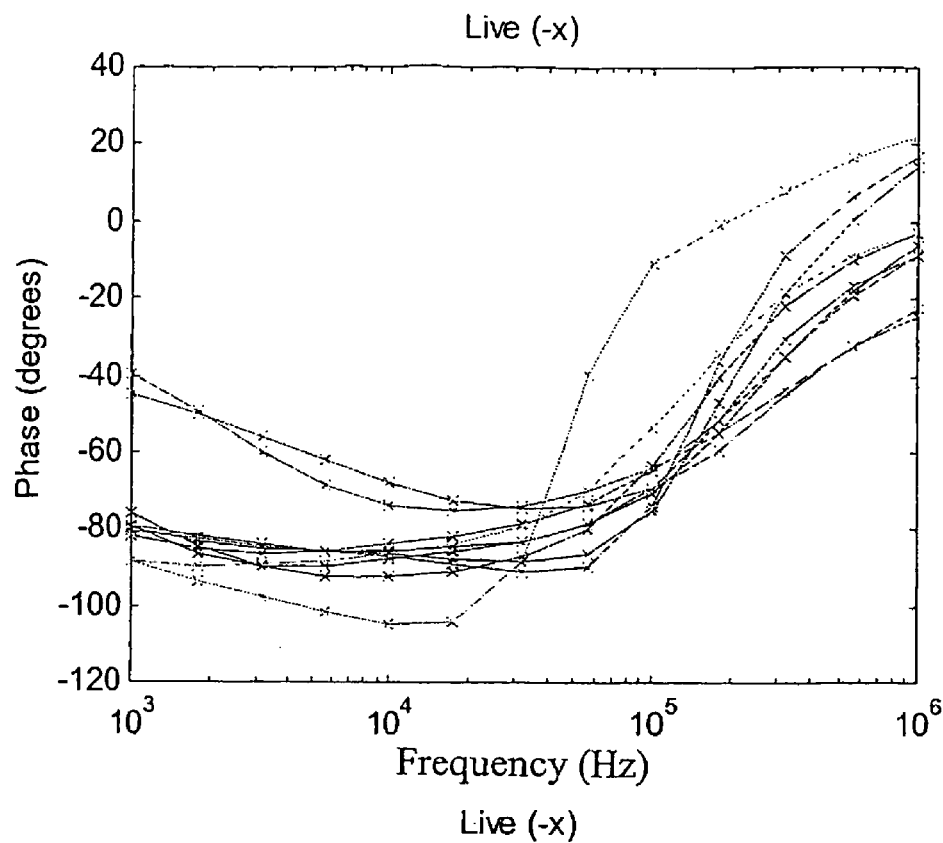
FIG. 5 shows the measured impedance phase as a function of frequency for a first electrode configuration.
Figure 6:
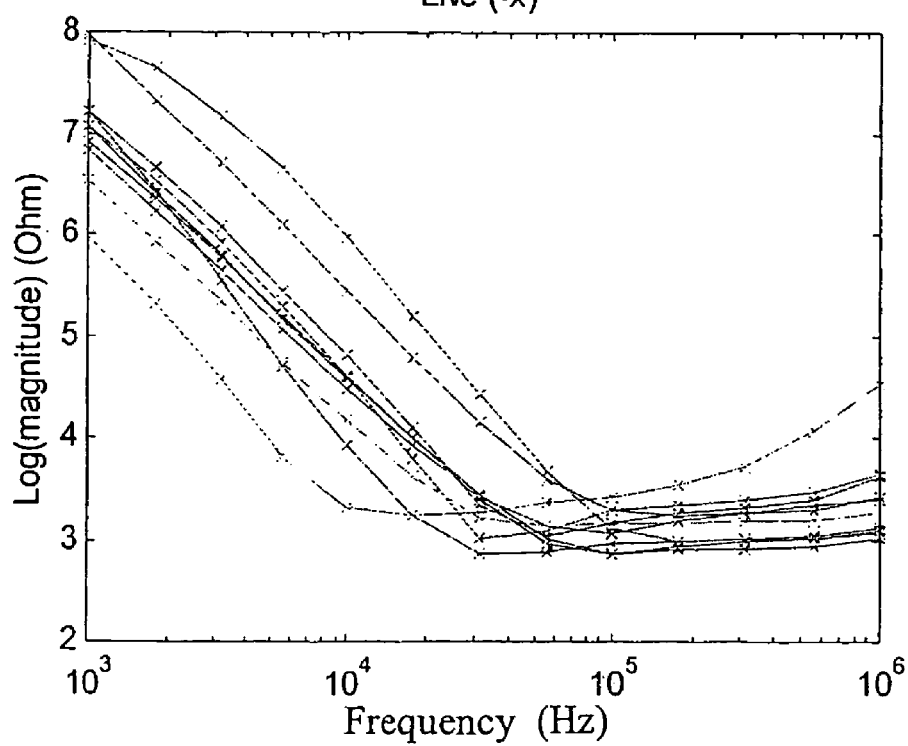
FIG. 6 shows the measured impedance absolute value as a function of frequency for a second electrode configuration.
Figure 7:
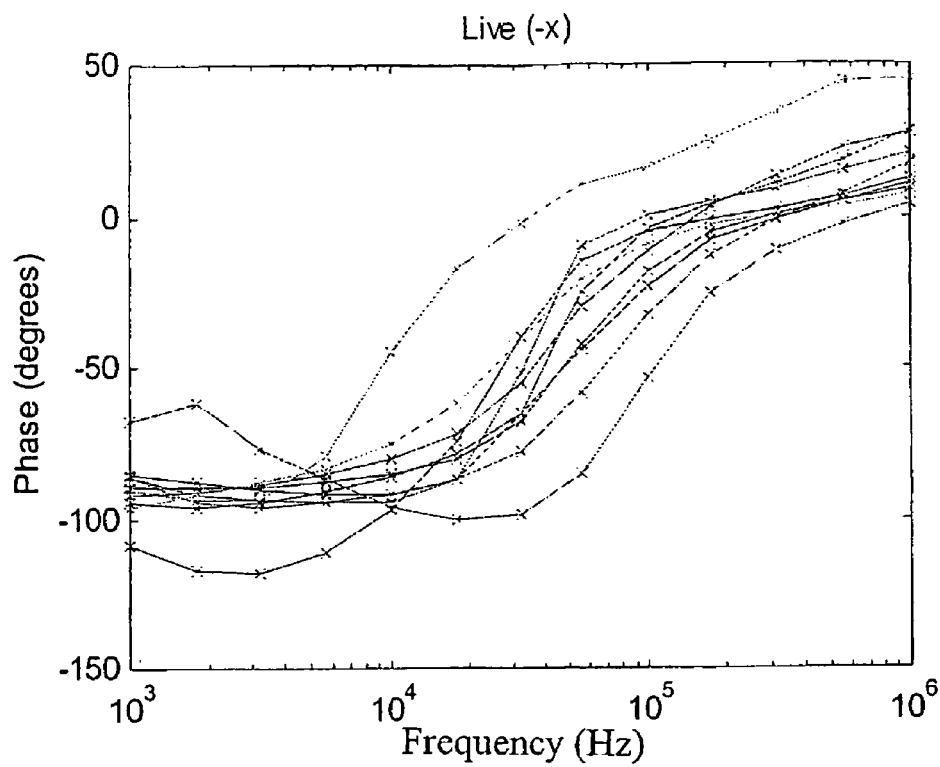
FIG. 7 shows the measured impedance phase as a function of frequency for a second electrode configuration.

FIGS. 4-7 show the measured magnitude and phase of the impedance for a number of live fingers from different persons, for two different electrode configurations. FIGS. 4 and 5 refer to one electrode configuration while FIGS. 6 and 7 refer to another.

A strong positive shift in phase is observed for both configurations. It is also observed that the impedance curve is essentially flat above the frequency of phase transition.

A similar phenomenon is not observed for any other substance we have tested. A so strong phase shift is not observed when the finger is measured using only two-point impedance measurements. Thus this is a possible criteria for determining the validity of a finger.

Figure 8:
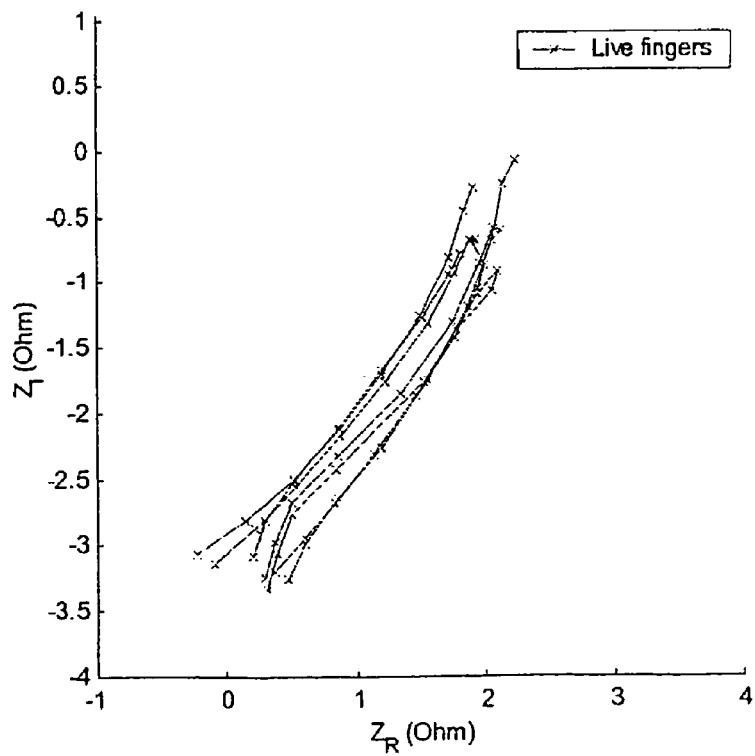
FIG. 8 shows a plot the real and imaginary part of the measured 4-point impedance for a number of live fingers with frequency as a parameter.

Properties of this frequency shift, such as its magnitude and its transition frequency, can be characterized in a number of different ways. For instance, the measured, complex impedance can be plotted as a function of frequency, i.e. by plotting the phase and magnitude against the frequency or by plotting the imaginary part against the real part with frequency as a parameter, see FIG. 8. In this figure a possible analysis for identifying live finger is illustrated, in showing the imaginary and real parts of the measured impedances $Z_I$ and $Z_R$. As mentioned above the slope, centre of gravity or lengths of these curves are some possible parameters for identifying a live finger. In a preferred embodiment the slope is used as a basis for live finger confirmation.

The advantage of the latter method is that the curve will look similar for different fingers even if the transition point occurs for quite different frequencies.

Certain characteristic of these curves, such as curve derivative, length, "center of mass", specific transition frequencies or the frequency when the curve approaches a certain value, may then be derived by an automatic computing unit and used as live finger identification parameters. The skilled engineer will be familiar with that the same measured properties can be presented in a number of different ways of which many are equivalent mathematically.

It has also been observed that the typical shift frequency changes when the distance between the electrodes increase. This is because a larger distance in general gives a higher measuring depth in the finger, and that the electrical properties of the finger vary with depth. This is visualized by comparing the curves in FIGS. 4 and 5, corresponding to a short electrode distance, with those of FIGS. 6 and 7 (longer electrode distance). In FIGS. 4 and 5 the typical transition frequency is much lower than in FIGS. 6 and 7.

The measured shift in transition frequency with electrode distance, which is very characteristic for live fingers, can be represented parametrically, and this or these parameters can be used to improve the live finger identification model.

It is seen from FIG. 4-7 that the actual transition frequency varies from person to person. This may be due to variations in humidity level or stratum corneum thickness, and may be corrected for by measuring across a larger interval of frequency, or by measuring at several different electrode distances. As seen by the curves, increasing the frequency has approximately the same effect on the phase as increasing the electrode distance. Around the transition frequency, an increase in frequency or electrode distance will generally increase the phase for live fingers. This very specific relationship between electrode distance and phase can be modeled mathematically and used as yet another criterion for identifying a live finger.

Figure 3:
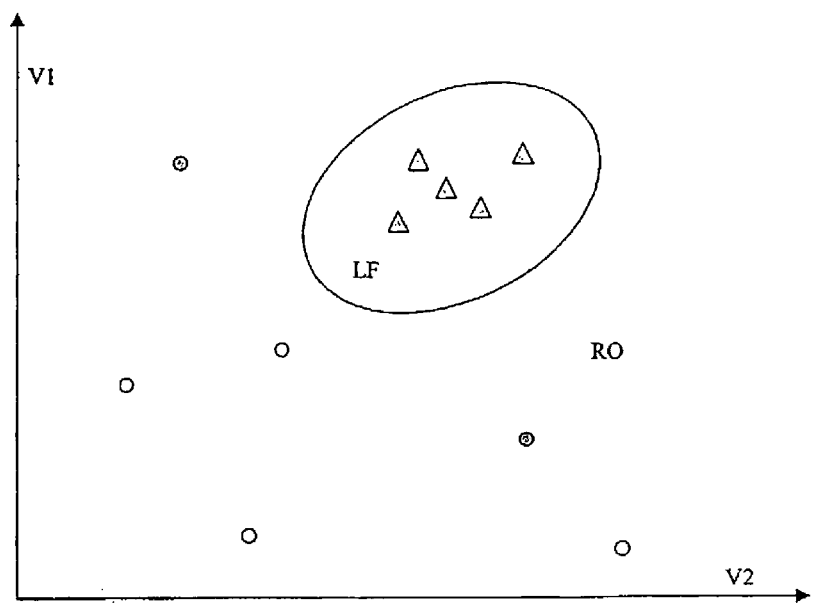
FIG. 3 illustrates a multivariate model to distinguish between live fingers and other objects. Note that if only one of the variables (either variable one or variable 2) is used, some of the "false fingers" (marked with red) are likely to be mistaken for real fingers.

Preferably, the criterion for accepting a live finger is based on the measurement of more than one parameter. A set of relevant parameters or variables can e.g. be found by feeding obtained impedance data into a multivariate model as illustrated in FIG. 3. The set of parameters according to a preferred embodiment be the impedance data illustrated in FIG. 8.

Through statistical analysis of measured data from live and fake fingers such a model will output a set of weighted, combined variables (typically two or three) that are optimized for distinguishing real from fake fingers. The model thus comprising chosen deviation limits within the data set, being sufficient to distinguish the real, dead and fake fingers.

Preferably, the variables should be normalized using any available methods, so as to avoid influences from varying sensor characteristics etc., and statistically independent.

The electrode configuration to be used for obtaining the desired variables will preferably be determined by the signal processing system based on measurements on several of the electrode configurations. This may be obtainable using several different electrodes, e.g., as mentioned above in a finger print scanner, but also related so other systems comprising a number of electrodes for performing measurements on skin.

A possible alternative solution to the variation of sensor combinations discussed above is that one configuration is measured at a time until the measurements match the given criterion, and after this concluding or switching to a second configuration. Measurements obtained from different electrode configurations may also be combined.

Two-point impedance data or other measurements on the finger (e.g. temperature) may be used in combination with the four-point data to enhance the selectivity towards fake or dead fingers. Only objects where all the specified variables fall within certain limits will be deemed a live finger. Other objects will be rejected.

This is shown schematically in the FIG. 3 for a model with two variables, where only objects that fall within the indicated oval area (obtained data shown as triangles) are considered live. The circles outside the oval correspond to data for rejected objects.

In summary, the preferred method, which requires not only one specific value but a set of variables to be within certain limits, will make it extremely difficult to construct a "false finger" material. On its side, dead fingers will be rejected due to biological processes taking place in the finger after death, changing the electrical parameters.

The invention claimed is:

1. Sensor assembly for determining the condition of a structure, especially for confirming if a measured fingerprint is on a live finger, by measuring characteristics of close to the structure surface, the sensor comprising:

a current source;

at least four electrodes at chosen positions relative to each other, said positions providing at least two relative distances between the electrodes, wherein a chosen first pair of said at least four electrodes constitutes current supply electrodes, and a chosen second pair of said at least four electrodes constitutes pickup electrodes, and of which at least one does not constitute a current supply electrode;

a measuring instrument coupled to said at least four electrodes for measuring the impedance between said chosen pair of pickup electrodes for providing a value characterizing the structure;

wherein said sensor is adapted to store a predetermined set of values characterizing a chosen condition for said structure;

wherein said sensor is adapted to compare said characteristics from each of said at least one pair of pickup electrodes with said set of predetermined values for detecting if said structure is in a certain condition, and the sensor assembly is adapted to alternating coupling of at least one current supply and measuring instrument to different electrode pairs with different distances between them, for measuring characteristic values at different depths in said structure; and wherein the supplied current is oscillating within a chosen frequency range and said sensor is adapted to measure the impedance at each pickup electrode and to compare the imaginary and real parts of the impedance signals as functions of the applied frequency, by determining the slope of the resulting curve, and to compare this slope with a predetermined set of slopes indicating a live finger.

2. Sensor assembly for determining the condition of a structure, especially for confirming if a measured fingerprint is on a live finger, by measuring characteristics of close to the structure surface, the sensor comprising:

a current source;

at least four electrodes at chosen positions relative to each other, said positions providing at least two relative distances between the electrodes, wherein a chosen first pair of said at least four electrodes constitutes current supply electrodes, and a chosen second pair of said at least four electrodes constitutes pickup electrodes, and of which at least one does not constitute a current supply electrode;

a measuring instrument coupled to said at least four electrodes for measuring the impedance between said chosen pair of pickup electrodes for providing a value characterizing the structure;

wherein said sensor is adapted to store a predetermined set of values characterizing a chosen condition for said structure;

wherein said sensor is adapted to compare said characteristics from each of said at least one pair of pickup electrodes with said set of predetermined values for detecting if said structure is in a certain condition, and the sensor assembly is adapted to alternating coupling of at least one current supply and measuring instrument to different electrode pairs with different distances between them, for measuring characteristic values at different depths in said structure; and wherein the pickup electrodes are constituted by sensor elements in a fingerprint sensor array.

3. Sensor assembly for determining the condition of a structure so as to confirm whether the structure is constituted by skin and living tissue, the sensor assembly comprising:

at least four electrodes, of which at least two electrodes constitute current supply electrodes which are connected to a current source for providing a current or voltage to said structure, and at least two electrodes constitute pickup electrodes of which at least a first pickup electrode is connected to a measuring instrument for measuring at least one parameter value relating to the impedance of the structure; and wherein said sensor assembly is adapted to alter which electrodes constitute current supply electrodes and/or which electrodes constitute pickup electrodes between different measurements so as to alter the distance(s) between the current supply electrodes and/or the pickup electrodes to thereby alter the depths of the structure at which the measurements are performed; and wherein said sensor assembly is further adapted to (1) store a predetermined set of values characteristic of at least one certain condition of the structure, and (2) compare the at least one measured parameter value with the predetermined set of values for determining whether the structure is in said certain condition, and wherein the distance between a first of said current supply electrodes and said first pickup electrode is less than 1 mm.

4. Sensor assembly for determining the condition of a structure so as to confirm whether the structure is constituted by skin and living tissue, the sensor assembly comprising:

at least four electrodes, of which at least two electrodes constitute current supply electrodes which are connected to a current source for providing a current or voltage to said structure, and at least two electrodes constitute pickup electrodes of which at least a first pickup electrode is connected to a measuring instrument for measuring at least one parameter value relating to the impedance of the structure; and wherein said sensor assembly is adapted to alter which electrodes constitute current supply electrodes and/or which electrodes constitute pickup electrodes between different measurements so as to alter the distance(s) between the current supply electrodes and/or the pickup electrodes to thereby alter the depths of the structure at which the measurements are performed; and wherein said sensor assembly is further adapted to (1) store a predetermined set of values characteristic of at least one certain condition of the structure, and (2) compare the at least one measured parameter value with the predetermined set of values for determining whether the structure is in said certain condition, and wherein said sensor assembly is further adapted to interchange the roles of the electrodes such that the roles of the pickup and supply electrodes may change sequentially for varying the relative positions between the sensors and thus the measured characteristics of the surface, and wherein said sensor assembly is further adapted to measure the phase of the signal at each pickup electrode, and to compare the distance between the pick up and supply electrode at chosen frequencies with the corresponding phase of the signal, and to compare these parameters with a predetermined set indicating a live finger.

* * * * *